US012678397B2

(12) United States Patent
Lee et al.

(10) Patent No.: US 12,678,397 B2
(45) Date of Patent: Jul. 14, 2026

(54) COSMETIC COMPOSITION COMPRISING LYCIUM CHINENSE MILL FERMENTATION EXTRACT AND GREEN TEA FERMENTATION EXTRACT, AND METHOD FOR MANUFACTURING SAME

(71) Applicant: DAEBONG LS CO., LTD., Incheon (KR)

(72) Inventors: Hye-Ja Lee, Seogwipo-si (KR); Ji Hye Kim, Seogwipo-si (KR); Tae-Heon Oh, Jeju-si (KR); Yun Kim, Seoul (KR); Jin Oh Park, Seoul (KR)

(73) Assignee: DAEBONG LS CO., LTD., Incheon (KR)

( * ) Notice: Subject to any disclaimer, the term of this patent is extended or adjusted under 35 U.S.C. 154(b) by 421 days.

(21) Appl. No.: 18/250,994

(22) PCT Filed: Jul. 9, 2021

(86) PCT No.: PCT/KR2021/008766

§ 371 (c)(1),
(2) Date: Apr. 28, 2023

(87) PCT Pub. No.: WO2022/092486

PCT Pub. Date: May 5, 2022

(65) Prior Publication Data

US 2024/0000699 A1 Jan. 4, 2024

(30) Foreign Application Priority Data

Oct. 30, 2020 (KR) ........................ 10-2020-0142893

(51) Int. Cl.
*A61K 8/9789* (2017.01)
*A61Q 19/02* (2006.01)
*A61Q 19/08* (2006.01)

(52) U.S. Cl.
CPC ............ *A61K 8/9789* (2017.08); *A61Q 19/02* (2013.01); *A61Q 19/08* (2013.01); *A61K 2800/522* (2013.01); *A61K 2800/85* (2013.01)

(58) Field of Classification Search
CPC ................................ A61K 8/9789; A61Q 5/00
See application file for complete search history.

(56) References Cited

FOREIGN PATENT DOCUMENTS

| | | | | | |
|---|---|---|---|---|---|
| JP | 2016-067248 | A | | 5/2016 | |
| KR | 10-2009-0123458 | A | | 12/2009 | |
| KR | 20100030368 | A | * | 3/2010 | ............. A61Q 19/08 |
| KR | 20110062212 | A | * | 6/2011 | ............... A61Q 7/00 |
| KR | 10-2011-0117876 | A | | 10/2011 | |
| KR | 10-2017-0020578 | A | | 2/2017 | |
| KR | 10-2017-0142334 | A | | 12/2017 | |
| KR | 20190091162 | A | * | 8/2019 | ........... A61K 8/9789 |

OTHER PUBLICATIONS

Liu, Y. et al. "Fermentation by Multiple Bacterial Strains Improves the Production of Bioactive Compounds and Antioxidant Activity of Goji Juice", Molecules, 2019, 24, 3519; https://doi.org/10.3390/molecules24193519. (Year: 2019).*

English Translation of the International Search Report in PCT/KR2021/008766, mailed Nov. 3, 2021.

Cho et al., "Antioxidative activity and Angiotensin Converting Enzyme Inhibitory activity of Fermented Medical Plants (DeulBit) and Its Modulatory Effects of Nitric Oxide Production," Journal of Applied Biological Chemistry 53(2): 91-98 (2010), English Abstract attached.

* cited by examiner

*Primary Examiner* — Gina C Justice
(74) *Attorney, Agent, or Firm* — MEDLER FERRO WOODHOUSE & MILLS PLLC

(57) ABSTRACT

The present invention relates to a cosmetic composition including a *Lycium chinense* mill ("Goji berry") fermented extract and/or green tea fermented extract, and a method for preparing the same. Specifically, there is provided a cosmetic composition with excellent antioxidant, wrinkle improvement and whitening effects, and a method for preparing the same.

4 Claims, 2 Drawing Sheets

COSMETIC COMPOSITION COMPRISING LYCIUM CHINENSE MILL FERMENTATION EXTRACT AND GREEN TEA FERMENTATION EXTRACT, AND METHOD FOR MANUFACTURING SAME

TECHNICAL FIELD

The present invention relates to a cosmetic composition including a *Lycium chinense* mill ("Goji berry") fermented extract and a green tea fermented extract, and a method for preparing the same. Specifically, the present invention relates to a cosmetic composition having excellent antioxidant, anti-wrinkle and whitening effects, which includes a Goji berry fermented extract and a green tea fermented extract, and a method for preparing the same.

BACKGROUND

One of the representative causes of skin troubles is free radicals existing in the human body, which destroy cells, cut connective tissues in a dermal layer of the skin, or cause cross-linking. As a result, it causes various problems such as skin wrinkle formation, skin cancer, cell death, rheumatoid arthritis, atopic dermatitis, acne and the like. These free radicals are generated by phagocytosis of leucocytes, electron transport system, metabolic processes, stress, pollutants, bacteria, and the like during ATP generation in mitochondria. Of course, in the human body, there are antioxidants (radical scavengers) such as superoxide dismatase (SOD), catalase, vitamin E, vitamin C, ubiquinol, and the like, but these antioxidants are broken by aging, pollution, UV, stress, etc., and thus free radicals are gradually increased.

Another major cause of skin troubles is the inflammatory reaction. Inflammation is a physiological reaction that protects the living body from harmful surrounding environments, that is, the intrusion of foreign substances such as bacteria and mechanical damage. Such inflammation increases many types of polymorphonuclear leukocytes (PMNs) and immune substances, and these cells treat and defend by secreting various types of proteolytic enzymes and cytokines, which are inflammatory cell products. In particular, enzymes such as elastase, hyaluronidase, and lipoxygenase break down proteins and lipids produced during inflammation, but their action may also sometimes cause harmful damage in adjacent tissue cells and non-cellular components.

Therefore, inflammation returns to normal function after the initial state has passed under certain conditions, but if a stimulant promoting inflammation is not removed or is continuously made, chronic inflammation occurs, hence causing more serious tissue damage. As a result, cells and connective tissues are damaged by proteolytic enzymes caused by excessive inflammation, and such damage of the connective tissue reduces skin elasticity and causes wrinkles, and furthermore, bad effects on cell regeneration and proliferation, hence leading to rapid skin aging. Therefore, in order to improve skin troubles, it is necessary to develop a cosmetic raw material that has excellent free radical scavenging ability and can quickly soothe the skin.

REFERENCES

Patent Document (Patent Document 1) Korean Patent Laid-Open Publication No. 10-2017-0142334

SUMMARY OF INVENTION

Problems to be Solved by Invention

In order to solve the above problems, an object of the present invention is to provide a cosmetic composition which is excellent in antioxidant, skin wrinkle improvement, whitening and skin soothing effects.

Another object of the present invention is to provide a method for preparation of the cosmetic composition.

Means for Solving Problems

In order to achieve the above objects, the present invention provides a cosmetic composition including a *Lycium chinense* mill ("Goji berry") fermented extract and a green tea fermented extract.

Goji berry in the present invention may be a leaf or fruit of a wolfberry tree, and green tea may be a green tea leaf.

The cosmetic composition may include Goji berry fermented extract and green tea fermented extract in a volume ratio of 6:4 to 9.9:0.1, and preferably 7:3 to 9.5:0.5. When it is beyond the above range, any one or more of antioxidant, skin wrinkle improvement, whitening and skin soothing effects may be reduced.

The Goji berry fermented extract and green tea fermented extract may be fermented with yeast. The yeast may be any one or more selected from *Saccharomyces cerevisiae, Saccharomyces boulardii, Saccharomyces* ellipsoids or *Schizosaccharomyces ellipsoids*, and preferably *Saccharomyces cerevisiae.*

The cosmetic composition according to the present invention is not particularly limited, but is preferably used for any one or more of antioxidant, anti-aging, skin wrinkle improvement, whitening, and skin soothing functions.

Further, the cosmetic composition may include any one formulation selected from the group consisting of a softening lotion, a nourishing lotion, a massage cream, a nourishing cream, a moisture cream, a hand cream, a foundation, an essence, a nourishing essence, a cream, a soap, a cleansing foam, a cleansing lotion, a cleansing cream, a body lotion, a body cream and a pack, but it is not limited thereto.

According to the present invention, a method for preparing a Goji berry fermented extract and/or a green tea fermented extract may include the following steps of:

(a) performing hot water extraction of Goji berry and/or green tea and filtering the same to obtain an extract;

(b) inoculating the extract with a carbon source and yeast to conduct fermentation; and (c) removing bacteria from the fermented product to obtain a Goji berry extract and/or a green tea extract.

Step (a) is a hot water extraction step of Goji berry and/or green tea using water as a solvent. The Goji berry and/or green tea may preferably be dried, but it is not limited thereto.

The hot water extraction is performed at 50 to 70° C., preferably at 60° C. for 60 to 120 minutes, and more preferably for 90 minutes. If it is less than the above temperature and time, active ingredients may not be sufficiently extracted. On the other hand, when it exceeds the above temperature and time, impurities may be extracted together or the active ingredients may be destroyed.

The carbon source in step (b) is not particularly limited, but may be saccharides, and specifically, monosaccharides including glucose, fructose, and galactose; disaccharides including maltose, sucrose and lactose; polysaccharides including starch, glycogen, and dietary fiber; and oligosaccharides.

The carbon source may be administered in an amount of 3 to 7% by weight ("wt. %"), and preferably 5 wt. % based on a weight of the extract. When administered with the amount less than the above range, activity of a strain to be inoculated afterward may be inhibited. On the other hand, when administered with the amount exceeding the above range, the strain may be overactive.

Yeast may be inoculated in an amount of 0.01 to 5 wt. %, and preferably 0.05 to 1.5 wt. % based on the weight of the extract. When it is less than the above range, fermentation may not proceed well. On the other hand, when it exceeds the above range, the fermentation may proceed excessively and not exhibit desired effects. The fermentation may be conducted at room temperature (15 to 30° C.), preferably at 25 to 28° C. for 2 to 5 days, and more preferably for 3 to 4 days. If it is beyond the above temperature, there is a fear that fermentation may not be performed well. On the other hand, if it is beyond the above fermentation period, it may not exhibit efficacy.

Advantageous Effects

According to the present invention, there are provided a cosmetic composition including a Goji berry fermented extract and a green tea fermented extract, and a method for preparing the same. Specifically, there may be provided a cosmetic composition with excellent antioxidant, anti-wrinkle and whitening effects, as well as a method for preparing the same.

MODE FOR CARRYING OUT INVENTION

Hereinafter, the present invention will be described in detail by way of examples and experimental examples.

However, the following examples and experimental examples are merely illustrative of the present invention, and the content of the present invention is not limited to the following examples and experimental examples.

Comparative Examples 1 to 3, Examples 1 to 5

Preparation of Goji Berry Extract and Green Tea Extract

After mixing dried Goji berries and/or green tea leaves in the mass ratio shown in the table below, purified water was added to 20 times the volume of Goji berries and green tea leaves, followed by extraction with hot water at 60° C. for 90 minutes to obtain an extract from which Goji berries and green tea leaves were removed.

In Examples 1 to 5, the extract was inoculated with a carbon source (sucrose, 5 wt. % based on the weight of the extract) and 0.1 wt. % of yeast (*Saccharomyces cerevisiae*) relative to the weight of the extract, and fermented at 25 to 28° C. for 3 to 4 days. Thereafter, bacteria were removed, and Goji berry fermented extract and green tea fermented extract were obtained.

TABLE 1

| Division | Goji berry | Green tea |
|---|---|---|
| Comparative Example 1 | 100 | |
| Example 1 | 100 | |
| Comparative Example 2 | | 100 |
| Example 2 | | 100 |
| Example 3 | 50 | 50 |
| Example 4 | 70 | 30 |
| Comparative Example 3 | 90 | 10 |
| Example 5 | 90 | 10 |

Experimental Example 1

BCA Protein Assay

Bicinchoninic acid (BCA) protein assay is a method to quantify a concentration of the entire protein in a sample. A peptide bond of the protein allows a reductive reaction of copper divalent ions (Cu2+) in alkaline environments to form copper monovalent ions (Cu+), and may form a complex with two BCA molecules to create purple color. In this regard, an absorbance may be measured at 562 nm.

<Principle of BCA Protein Assay>

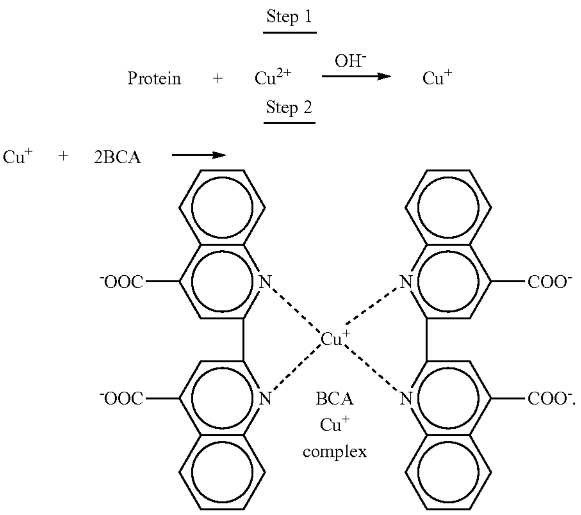

For BCA protein assay, Pierce BCA Protein Assay Kit (Thermo, USA) was used. By mixing Reagent A and Reagent B in a ratio of 50.1 in a kit, WR was prepared. Then, 2 ml of the prepared WR was admixed in 100 µl of sample and standard and reacted at room temperature for 2 hours. The absorbance was measured at 562 nm after dispensing 200 µl of the reaction product into a 96-well plate.

TABLE 2

| Sample | Protein (µg/ml) |
|---|---|
| Comparative Example 3 | 15375 |
| Example 5 | 30125 |

Figure 1:
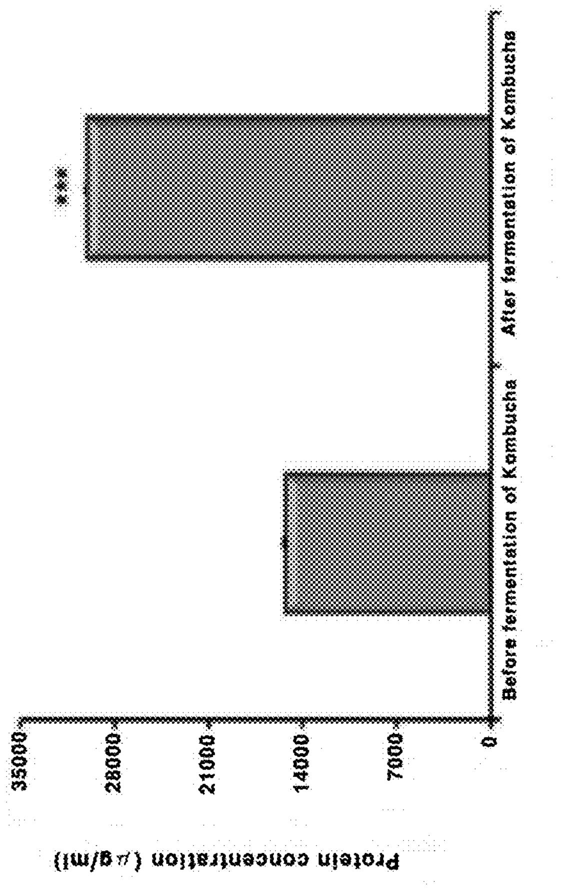
FIG. 1 shows results of BCA protein assay of the extract according to the present invention.

As a result of the experiment, when compared varied amounts of protein before and after fermentation of kombucha, it was confirmed that the protein was increased by about 2 times or more (FIG. 1).

Experimental Example 2

Assessment of Antioxidant Efficacy (Measurement of DPPH Free Radical Scavenging Activity)

DPPH is a purple compound that exhibits unique absorption at 515 to 520 nm as an oxidant which is itself a very stable free radical. When it comes into contact with a substance having antioxidant activity, the radical is removed and purple color is bleached whereby the activity of the antioxidant substance can be measured according to an extent of discoloration. This experiment is an experiment in which oxidation is firstly initiated with DPPH, followed by determining a scavenging activity measurement ability for radicals by a sample.

Electron donating ability (EDA %) of each sample extract was measured according to the DPPH free radical scavenging method through Blosis method (Blois, 1958). Specifically, each sample extract was prepared at different concentrations by dissolving it in methanol, and dispensed by 100 μl into a 96-well plate. Then, an equal amount of 0.4 mM DPPH dissolved in ethanol was added, followed by leaving the solution in a dark room at room temperature for 30 minutes. Thereafter, using an ELISA Reader, an absorbance at 515 nm was measured. As a positive control, L-ascorbic acid, quercetin, and butylated hydroxy anisole (BHA) were prepared by concentration, respectively, and absorbances thereof were measured and compared with the above sample. The lower the absorbance of the reaction mixture, the higher the free radical scavenging ability. DPPH free radical scavenging activity was calculated from the following equation, and antioxidant ability was expressed as a reducing power by electron donating capacity (EDA %). Further, for comparing and reviewing the antioxidant ability, a concentration of the sample (SC50) appearing when the absorbance of DPPH is lowered by 50% was measured and used for calculation of the DPPH free radical scavenging activity in the equation below. After repeating the experiment three times for each sample, an average value thereof was obtained.

$$\text{DPPH free radical scavanging activity (\%)}=(A\text{control}-A\text{sample})/A\text{control}\times 100$$

Asample=absorbance of reaction solution added with sample

Acontrol=absorbance of reaction solution added with methanol instead of sample

TABLE 3

| Sample classification | | DPPH radical scavanging |
|---|---|---|
| Sample name | Concentration (%) | activity (%) |
| Untreated group | | 0.00 |
| Comparative Example 1 | 2.5% | 39.92 |
| Example 1 | 2.5% | 45.90 |
| Example 3 | 2.5% | 54.36 |
| Example 4 | 2.5% | 45.04 |
| Comparative Example 3 | 2.0% | 50.4 |
| Example 5 | 2.5% | 88.2 |
| | 10% | 107.17 |

As a result of the experiment, Example 1 in which the Goji berry extract was fermented had DPPH radical scavenging ability slightly higher than or similar to Comparative Example 1 in which the Goji berry extract was not fermented, whereas Comparative Examples 3 and 5 showed that the fermented product had significantly higher radical scavenging ability than the extract. Further, it was confirmed that the scavenging ability was improved in a concentration-dependent manner. This is presumed because the green tea and Goji berry fermented products of the present invention generate synergistic effects at a specific composition ratio.

Experimental Example 3

Assessment of Wrinkle Improvement Efficacy (Elastase Inhibition Assay)

Elastase, known as an enzyme to decompose elastin that is an elastic fiber, exists in healthy skin with a low concentration. In the case of skin inflammatory reaction, a concentration of elastase may be increased rapidly. Such elastase is known as an enzyme that is the main cause of wrinkles formed by decomposing elastin, which is an elastic fibrous protein, and thus breaking a mesh of dermal tissues in the skin. Further, the activity of the elastase is lowered, whereby skin aging may be inhibited. Accordingly, through experiments of the elastase activity inhibitory ability, skin wrinkle improvement effects of the extract can be supported. In order to determine the elastase inhibitory activity, an amount of p-nitoanilide produced using N-succinyl-Ala-Ala-Ala-p-nitroanilide (sigma) as a substrate was measured.

Elastase inhibition assay was performed as follows: 20 uL of sample was added to 0.2M Tris-HCl buffer (pH8.0), then 20 uL of substrate was added thereto, followed by reacting the mixture at 25° C. for 10 minutes and then adding 20 uL of 1 unit elastase. Following this, the reaction mixture was reacted at 25° C. for 15 minutes, and then cooled to stop the reaction, followed by measuring an absorbance at 405 nm.

$$\text{Elastase inhibitory activity (\%)}=(1-A\text{sample}/A\text{control})\times 100$$

Asample=absorbance of sample-added group

Acontrol=absorbance of no addition group

TABLE 4

| Sample classification | | Elastase inhibition |
|---|---|---|
| Sample name | Concentration (%) | rate (%) |
| Comparative Example 2 | 12.5% | 0.84 |
| Example 2 | 12.5% | 0.65 |
| Example 3 | 12.5% | 0.29 |
| Example 4 | 12.5% | 20.97 |
| Comparative Example 3 | 25% | −0.05 |
| | 50% | 14.75 |
| Example 5 | 12.5% | 30.97 |
| | 25% | 48.39 |
| | 50% | 84.50 |

As a result of comparing the elastase inhibition rates, green tea in both forms of the fermented product and the extract did not show inhibition rate. Further, in Examples 2, 3, 4 and 5, when the fermented product of Goji berry extract and the fermented product of green tea extract have a specific ratio at the same concentration, it showed an increase in inhibition rate. On the other hand, referring to Comparative Example 3 and Example 5, the fermented product had significantly higher elastase inhibitory effects than the extract even when these have the same composition ratio, and such inhibitory effects were increased in a concentration-dependent manner.

Experimental Example 4

Assessment of Whitening Efficacy (Tyrosinase Inhibition Assay)

The possibility of whitening effects could be inferred by evaluating the inhibitory activity of tyrosinase, which is an essential enzyme in a melanin synthesis process. Tyrosine is metabolized to DOPA and dopaquinone, which are precursors for melanin production by the enzyme tyrosinase. Therefore, tyrosinase inhibition may be expected to achieve skin whitening effects through regulation of melanin pigment in the skin. The tyrosinase inhibitory effects were measured using the dopachrome method. After mixing 50 μL of mushroom Tyrosinase-300 unit and 25 μL of 1.5 mM L-tyrosine or 75 μL of the sample, the absorbance was measured at a wavelength of 490 nm before incubation and after incubation for 15 minutes, respectively.

$$\text{Tyrosinase inhibitory activity (\%)}=(1-A\text{sample}/A\text{control})\times 100$$

Asample=absorbance of the sample-added group
Acontrol=Absorbance of no addition group

TABLE 5

| Sample classification | | Tyrosinase inhibition |
|---|---|---|
| Sample name | Concentration (%) | rate (%) |
| Comparative Example 2 | 12.5 | 21.99 |
| Example 2 | 12.5 | 19.96 |
| Example 3 | 12.5 | 14.95 |
| Example 4 | 12.5 | 10.61 |
| Comparative Example 3 | 12.5 | 18.84 |
| | 50 | 35.91 |
| Example 5 | 12.5 | 33.25 |
| | 50 | 48.88 |

Referring to Examples 2 to 4, the lower the ratio of the green tea fermented product, the lower the tyrosinase inhibition rate. On the contrary, in the case of comparing Example 4 and Example 5, when the ratio of the Goji berry extract fermented product and the green tea extract fermented product were increased from 7:3 to 9:1, the tyrosinase inhibition rate was rather increased.

[Experimental Example 5] Assessment of Skin Soothing Efficacy

Figure 2:
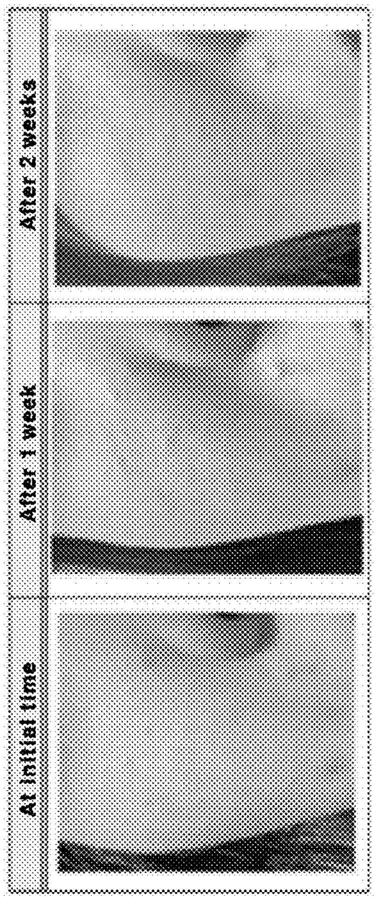
FIG. 2 shows results of evaluating the skin soothing effects of the extract according to the present invention.

In order to evaluate the skin soothing efficacy of the extract according to the present invention, the product of Example 5 was applied to the face with redness after washing in the morning and evening and, when completely absorbed into the skin, a process of applying the product to the face was repeated three or more times. As a result of the experiment, it was confirmed that the skin redness and red spots were decreased over time (FIG. 2).

The invention claimed is:

1. A cosmetic composition comprising a *Lycium chinense* mill ("Goji berry") fermented extract and a green tea fermented extract, wherein a relative volume ratio of the Goji berry fermented extract to the green tea fermented extract is about 7:3 to about 9:1.

2. The cosmetic composition according to claim 1, wherein the Goji berry fermented extract and the green tea fermented extract are fermented with any one or more of yeast selected from *Saccharomyces cerevisiae, Saccharomyces boulardii, Saccharomyces* ellipsoids, or Schzosaccharomyces ellipsoids.

3. The cosmetic composition according to claim 1, wherein the composition is used for any one selected from antioxidant, anti-aging, wrinkle improvement, whitening and skin soothing functions.

4. The cosmetic composition according to claim 1, wherein the composition has any one formulation selected from the group consisting of: a softening lotion, a nourishing lotion, a massage cream, a nourishing cream, a moisture cream, a hand cream, a foundation, an essence, a nourishing essence, a cream, a soap, a cleansing foam, a cleansing lotion, a cleansing cream, a body lotion, a body cream and a pack.

* * * * *